United States Patent
Mergemeier

(10) Patent No.: US 9,574,242 B2
(45) Date of Patent: Feb. 21, 2017

(54) **METHOD FOR DETECTING A METHICILLIN RESISTANT COAGULASE POSITIVE *STAPHYLOCOCCUS AUREUS* STRAIN**

(71) Applicant: Steffen Mergemeier, Berlin (DE)

(72) Inventor: Steffen Mergemeier, Berlin (DE)

(*) Notice: Subject to any disclaimer, the term of this patent is extended or adjusted under 35 U.S.C. 154(b) by 52 days.

(21) Appl. No.: 14/373,902

(22) PCT Filed: Jan. 23, 2013

(86) PCT No.: PCT/EP2013/051242
§ 371 (c)(1),
(2) Date: Jul. 23, 2014

(87) PCT Pub. No.: WO2013/110660
PCT Pub. Date: Aug. 1, 2013

(65) Prior Publication Data
US 2014/0370512 A1    Dec. 18, 2014

(30) Foreign Application Priority Data

Jan. 23, 2012  (EP) .................................... 12152157

(51) Int. Cl.
C12Q 1/68       (2006.01)
C12P 19/34      (2006.01)

(52) U.S. Cl.
CPC ......... *C12Q 1/689* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS 7,449,289 B2 * 11/2008 Huletsky ................ C12Q 1/689
                                                       435/6.15
8,442,924 B2 *  5/2013 Lu .......................... G06F 19/24
                                                       706/12

FOREIGN PATENT DOCUMENTS

EP      0887424 A2    12/1998
EP      1 529 847 A1   5/2005
WO      2002/099034 A2  12/2002
WO      2009/085221 A2   7/2009

OTHER PUBLICATIONS

Cuny et al., "PCR for the identification of methicillin-resistant *Staphylococcus aureus* (MRSA) strains using a single primer pari specific for SCCmec elements and the neighbouring chromosome-borne orfX," Clin. Microbiol. Infect., 2005, vol. 11, pp. 834-837.*
van der Zee et al., "Detection of novel chromosome-SCCmec variants in Methicillin Resistant *Staphylococcus aureus* and their inclusion in PCR based screening," BMC Research Notes, 2011, vol. 4, pp. 1-6.*
U. Reischl: "Single-nucleotide polymorphism in the SCCmec-orfX junction distinguishes between livestock-associated MRSA CC398 and human epidemic MRSA strains", in: Eurosurveillance, Dec. 10, 2009, pp. 1-8.

* cited by examiner

*Primary Examiner* — Young J Kim
(74) *Attorney, Agent, or Firm* — Joyce von Natzmer; Agris & von Natzmer LLP

(57) ABSTRACT

The invention relates to a method for detection of a methicillin resistant coagulase positive *Staphylococcus aureus* (MRSA) strain by means of a sequence specific amplification reaction.

17 Claims, 9 Drawing Sheets

Fig. 2

Figure 1:
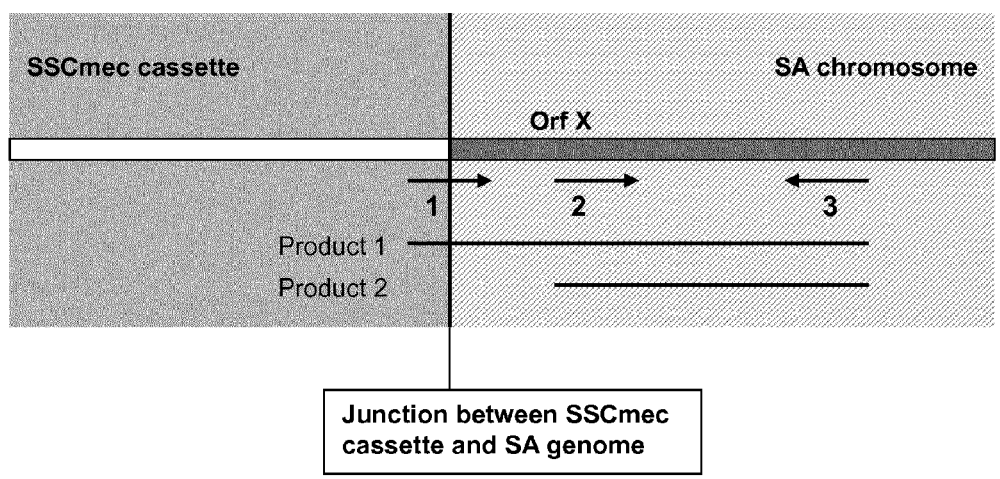

| Product | Primer | Channel | Figure |
|---|---|---|---|
| 1   SSCmec | 1 – 3 | 510 | 3 and 4 |
| 2   SA | 2 – 3 | 610 | 5 and 6 |
| 3   mecA | --- | 660 | 7 and 8 |

Fig. 9

```
AB014431 I (SEQ ID NO 12)
CATTACTTATGATAAGCTTCTCCAC GCATAAATCTTAAATGCTC TATACACTTGCTCAATTAACACAACC CGATCATTGATGTGGAATGTCATTTTGCTGAA TGATAGTGCGTAGTTACTGCGTTG

AB063172 II (SEQ ID NO 13)
CATCATTTATGATAGCTTCTCCAC GCATAAATCTTAAATGCTC TATACACTTGTTCAATTAACACAACC CGCATCATTGATGTGGAATGTCATTTTGCTAAA TGATAGTGCATAGTTACTGCGTTG

AB425427 III (SEQ ID NO 14)
TTTATTGTGTACGCTTCTCCAC GCATAAATCTTAAATGCTC TGTACACTTGTTCAATTAACACAACC CGGATCATTGATGTGGAATGTCATTTTGCTGAA TGATAGTGCGTAGTTACTGCGTTG

FR753166 IV (SEQ ID NO 15)
CATCACTTATGATACGCTTCTCCAC GCATAAATCTTAAATGCTC TATACACTTGCTCAATTAACACAACC CGCATCATTGATGTGGAATGTCATTTTGCTGAA TGATAGTGCGTAGTTACTGCGTTG

GQ902038 V (SEQ ID NO 16)
TTTTATTTATGATAGCTTCTCCAC GCATAAATCTTAAATGCTC TATACACTTGCTCAATTAACACAACC CGCATCATTGGTGTGAAATGTCATTTTGCTGAA TGATAGTGCGTAGTTACTGCGTTG

CATCATTTATGGTATGCTTCTCCAC
First Forward Primer (SEQ ID NO 1)

TGTACACTTGTTCAATTAACACAACC
Second Forward Primer (SEQ ID NO 2)

3-ACTATCACGTATCAATGACGCAAC-5
Reverse Primer (SEQ ID NO 3)
```

METHOD FOR DETECTING A METHICILLIN RESISTANT COAGULASE POSITIVE *STAPHYLOCOCCUS AUREUS* STRAIN

CROSS-REFERENCE TO RELATED APPLICATIONS

This is the U.S. national stage of International application PCT/EP2013/051242, filed Jan. 23, 20013 designating the United States and claiming priority to European application EP 12152157.9, filed Jan. 23, 2012.

INCORPORATION OF SEQUENCE LISTING

The sequence listing is provided as a file entitled "7014-1740-SEQ ST25.txt", created Aug. 31, 2016, which is 4 KB in size. The information in the electronic format of the Substitute Sequence Listing is incorporated herein by reference in its entirety.

The invention relates to a method for detection of a methicillin resistant coagulase positive *Staphylococcus aureus* (MRSA) strain by means of a sequence specific amplification reaction.

BACKGROUND OF THE INVENTION

*Staphylococcus aureus* (SA) has long been recognized as a human pathogen responsible for a wide range of afflictions. Since its first identification in the early 1960s methicillin-resistant *Staphylococcus aureus* (MRSA) has become one of the most significant pathogens worldwide and is capable of causing a wide range of hospital infections. *Staphylococcus aureus* infections can be lethal.

*Staphylococcus aureus* is part of the normal skin flora in healthy persons and is mainly found in the anterior nasal sinus, in the throat, the openings of the mammary glands and on the skin. However, it can cause severe infections when the general condition of the patient is weakened, for example after tissue injury or surgical intervention. SA is described as the most frequent cause of sepsis, skin and soft-tissue infections and pneumonia worldwide.

The ability of SA to adapting to rapidly changing environments was seen in the emergence of *Staphylococcus aureus* strains that acquired resistance mechanisms to a large number of antimicrobial agents shortly after the introduction of these drugs into clinical practice. Studies have sown that 97% of the *Staphylococcus aureus* isolates recovered carried resistance to penicillin. The introduction of methicillin in clinical practice was followed by the appearance of the first isolate of *Staphylococcus aureus* that was resistant not only to penicillin, streptomycin, and tetracycline, but also to methicillin.

The danger from methicillin resistant *Staphylococcus aureus* (MRSA) as a clinical pathogen is caused by the combination of the resistance gene, which provides resistance to methicillin-type antibiotics, with the particular protective mechanism provided by the enzyme coagulase.

A significant problem in diagnosing *Staphylococcus aureus* (SA) lies in the differentiation between methicillin resistant, coagulase positive MRSA and methicillin resistant, coagulase negative *Staphylococcus* (CNS) strains, and in particular in mixtures of such strains with and without resistance. Hence a diagnostic differentiation of CNS from *Staphylococcus aureus* is needed.

SA strains obtain methicillin resistance through the genomic integration of a gene-fragment, the SSCmec cassette, which in addition to other essential information exhibits the mecA gene, which is responsible for the phenotypical characteristics of resistance.

The SSCmec cassette is integrated at a highly conserved specific site of integration in the chromosomal DNA of SA. This conserved site is positioned close to the 3' end of an open reading frame (orf X) of the SA genome. It is of significant importance for the present invention that the integration side is highly conserved. However, at least ten various types of the SSCmec cassette with sequence variability have been described in the art.

Another significant problem that arises in mixed cultures of SA and CNS strains, which also may contain strains without the resistance cassette, is that the individual detection of the SA genome and detection of the mecA gene is not sufficient because these gene products may originate from separate individual organisms. Modern molecular diagnostic methods have therefore been developed for the detection of MRSA that preferably detect the junction between the SSCmec cassette and the SA genome.

Examples of such approaches towards detection of the junction between the SSCmec cassette and the SA genome are disclosed in EP 0887424, WO 2002/099034 and WO 2009/085221.

The methods disclosed in these documents relate to polymerase chain reaction (PCR) based methods, which utilize sequence specific primers that specifically hybridize to DNA sequences in the region flanking the cassette-genome junction, so that the target PCR product to be amplified is amplified across the cassette-genome junction.

The methods disclosed in the art do however exhibit significant disadvantages, whereby various false results maybe obtained. Such false results relate commonly to false positives and at times also to false negatives.

The main cause for false positive results is the significant similarity of the junction region of CNS strains with a resistance cassette, in comparison to the analogous junction region of the MRSA strains. Due to this sequence similarity CNS strains with resistance are falsely identified as MRSA. In light of the prior art, novel strategies (for example novel primer sequences) are required in order to avoid false positive identification of CNS. Sequences for primers have until the present time not been developed that enable reliable differentiation between the junction region of CNS strains with a resistance cassette, in comparison to the analogous junction region of the MRSA strains.

False positives may also occur when the junction region is successfully amplified but a deletion of the mecA gene in the integrated cassette has occurred.

The main cause for false negative results is the failure of multiplex primer systems directed towards the various integration sites due to the sequence variation in these regions. The DNA sequence of the SSCmec cassette close to the junction point varies between different MRSA strains. New strains with sequence variation in this region are being discovered regularly, all of which require new primer design and additional forward primers in multiplex reactions, leading to increased failure rates due to multiplex complexity and more expensive amplification reactions. Multiplex design is complicated and labor-intensive, requiring careful sequence selection for compatible melting temperatures of the oligonucleotides applied, whereby multiplex reactions may ultimately need to be avoided for additional security and reliability of the analysis, so that individual reactions should be applied in place of multiplex reactions, thereby leading to increased reagent usage and unwanted associated cost.

Figure 3:
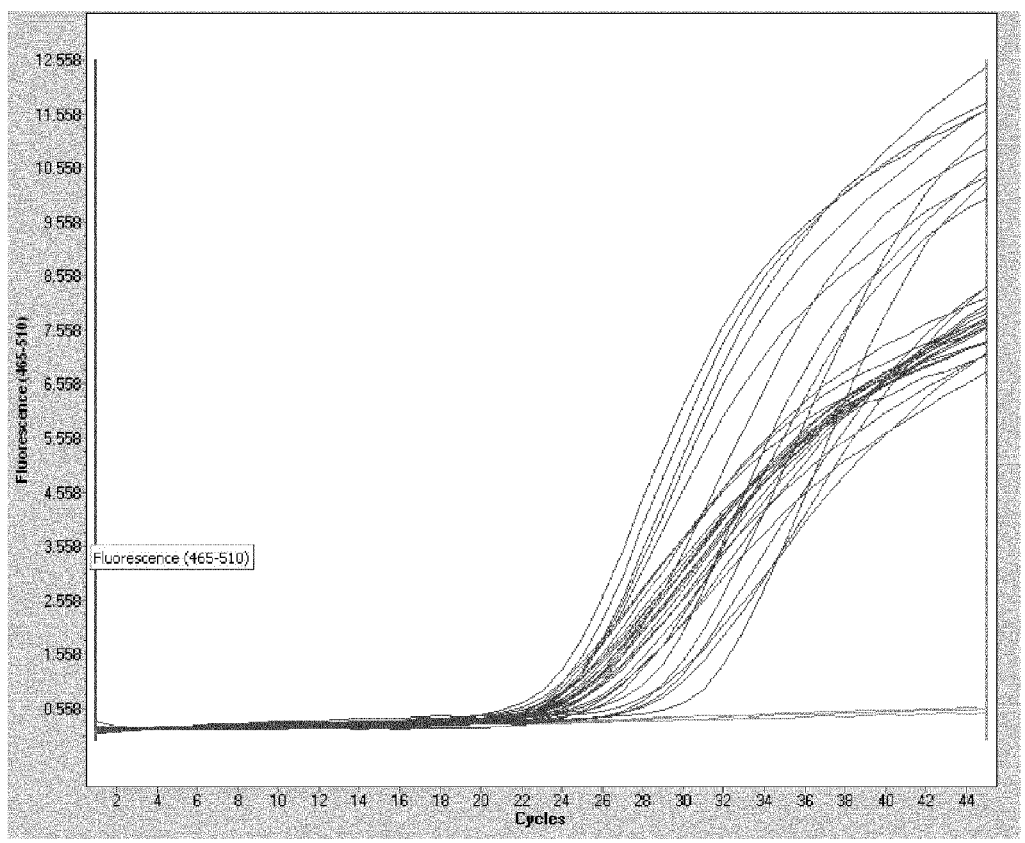
Figure 4:
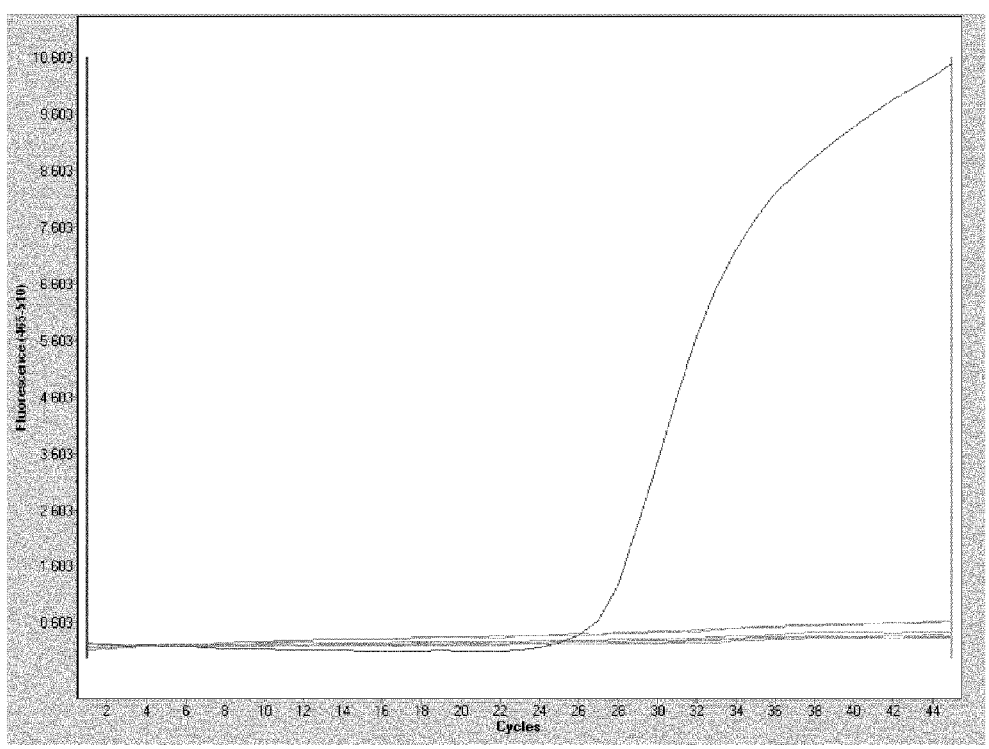

For example WO 2009/085221 discloses a method where various forward primers are to be applied within the SSCmec cassette depending on the strain to be interrogated. As can be seen in FIGS. 2 to 4 of WO 2009/085221, multiple forward primers are listed that must be either applied in multiplex or separate reactions, in order to provide sufficient screening of known MRSA strains.

In order to overcome these disadvantages more PCR reactions must be applied (often in complicated multiplex reaction systems) or the sensitivity of the system must be reduced. Neither of these potential solutions represents a satisfactory solution due to increased complexity (and subsequent increased frequency of failure) or lack of reliability.

PCR detection systems for MRSA have been described in the art that exhibit a primer that hybridizes across the junction between the SSCmec cassette and the SA genome (for example the primer is a single DNA oligonucleotide that binds both cassette and genome sequences). Such an approach was described in EP 1529847. However, the oligonucleotide primers described therein exhibit a significant disadvantage, namely, that the melting temperature (Tm) of the primers is approximately between 38 and 48° C., depending on the particular sequence and method used for calculation, resulting in an inability of this method to be effectively applied in practice. Low Tm of the primer causes significant problems in amplification due to the required low annealing temperature (Ta) applied during cycling. In order to enable annealing of a primer with low Tm (such as 48) to its template sequence, a very low Ta must be applied. Due to the low Ta non-specific products tend to amplify in great numbers caused by a high number of base pair mismatches. At low Ta the stringency regarding base pairing is significantly reduced, thereby allowing mismatch annealing and a large number of unspecific products. Mismatch tolerance at low Ta is found to have the one of the strongest influences on PCR specificity.

SUMMARY OF THE INVENTION

In light of the prior art the technical problem underlying the present invention is to provide a method for detection of a methicillin resistant *Staphylococcus aureus* (SA) strain that overcomes the disadvantages of those methods known in the prior art.

This problem is solved by the features of the independent claims. Preferred embodiments of the present invention are provided by the dependent claims.

Therefore, the invention relates to a method for detection of a methicillin resistant coagulase positive *Staphylococcus aureus* (MRSA) strain by means of a sequence specific amplification reaction, whereby the strain to be detected comprises a chromosomal *Staphylococcus* mec (SSCmec) cassette, which preferably carries a mecA gene, characterized in that one or more first forward primer(s), preferably 3, 2 or most preferably 1 forward primer, is used in the amplification reaction, of which the 5' end hybridizes to the target DNA sequence within the SSCmec cassette and the 3' end hybridizes in the adjacent chromosomal DNA, whereby the melting temperature (Tm) of the one or more first forward primer(s) is between 55° and 65° C., preferably between 56° and 64° C., more preferably between 57° and 63° C., or 58° and 62° C., or 59° and 61° C., and most preferably is 60° C.

The invention therefore relates primarily to an MRSA-identification method that employs a forward primer that hybridizes (or binds to) the template DNA region of the junction itself (and adjacent DNA sequences) across the boundary of mec (SSCmec) cassette and the SA genome (adjacent chromosomal DNA).

In a preferred embodiment the MRSA strain to be detected comprises a chromosomal *Staphylococcus* mec (SSCmec) cassette, which carries a mecA gene, or mecA-equivalent gene.

In one embodiment the method of the present invention is characterized in that the SA strain to be identified is selected from the group consisting of type I, II, III, V, IV a, IV b, IV c, VII, VIII, IX and/or X. In another preferred embodiment the method of the present invention is capable of detecting MRSA of type I, II, III, V, IV a, IV b, IV c, VII, VIII, IX and/or X, especially types I, II, III, V, IV a, IV b and/or IV c.

It is a surprising and advantageous aspect of the present invention that the present method enables detection of various MRSA strains in a reliable and efficient manner. In light of the prior art there is significant need in the field of MRSA diagnostics for amplification based approaches that are not overly sensitive to sequence variation present in different pathogenic MRSA strains discovered world wide. At the time of the present invention no noteworthy efforts had been disclosed in the art towards reducing the complexity of multiplex approaches by producing simplified methods to potentially identify multiple variants of MRSA simultaneously.

In a preferred embodiment of the invention multiple forward primers can be used in a multiplex manner, but preferably fewer forward primers are applied in the method than the number of MRSA variants that can potentially be tested. This feature of the invention enables simplifications in multiplex approaches, whereby until the present invention separate primer sequences have been developed and applied for each sequence variant to potentially be identified. The phrase "potentially be identified" or "tested" relates to the ability of the method to identify multiple MRSA variants, although not all variants must be detected. Each sample to be tested may only contain one particular MRSA strain, but the method of the invention enables the application of the same method without requiring modification to potentially identify various MRSA strains.

In one embodiment the method of the present invention is characterized in that the one or more first forward primer(s) according to claim 1 comprises or preferably consists of a sequence according to SEQ ID Nr. 1. It was a surprising and beneficial aspect of the invention that the particular preferred sequence of SEQ ID 1, in addition to closely related functionally analogous sequences as described herein, when present as an oligonucleotide, is capable of binding to the relevant template region of a broad range of MRSA sequence variants. As has been shown in the example 1 of the invention, amplification of the target DNA from various known and unknown MRSA strains with sequence variation in the template region (see FIG. 9) has been achieved (also FIG. 5). Unexpectedly, the sequence of SEQ ID No. 1 also exhibits improved stability during long term storage and exhibits a surprisingly high affinity for template sequences with varying sequence specificity.

Therefore, the invention relates to a method for detection of a methicillin resistant coagulase positive *Staphylococcus aureus* (MRSA) strain by means of a sequence specific amplification reaction, whereby the strain to be detected comprises a chromosomal *Staphylococcus* mec (SSCmec) cassette, characterized in that one or more first forward primer(s), preferably 3, 2 or most preferably 1 forward primer, is used in the amplification reaction, of which the 5' end hybridizes to the target DNA sequence within the SSCmec cassette and the 3' end hybridizes in the adjacent chromosomal DNA, whereby the forward primer comprises, preferably consists of, a sequence according to SEQ ID Nr. 1

In one embodiment the method of the present invention is characterized in that the one or more first forward primer(s) comprises a functionally analogous sequence, comprising a nucleotide sequence with more than 80% sequence identity, preferably more than 90% sequence identity, to SEQ ID Nr. 1, for example, 80, 81, 82, 83, 84, 85, 86, 87, 88, 89, 90, 91, 92, 93, 94, 95, 96, 97, 98, 99%. Functionally analogous sequences are those that although exhibiting differences in DNA sequence, so that for example the same, fewer or more mismatches may occur between primer and template, exhibit a similar Tm and/or binding specificities for the various MRSA strains with sequence variation, so that the function of the primer in the context of the present invention is maintained. Functionally analogous sequences can be tested by one skilled in the art without inventive effort in light of the information provided within the application, for example by testing Tm or hybridization properties in the context of the PCR or other amplification method described.

In one embodiment the method of the present invention is characterized in that a second forward primer is used in the amplification reaction, which hybridizes in the SA genome. This additional amplification enables the confirmation of *Staphylococcus aureus* (SA). Methods previously described in the prior art have provided no additional control for SA identification, whereby SCCmec cassettes or mecDNA integrated in other *Staphylococcus* species could also be identified. The second forward primer therefore provides a further identification of SA strains that provides concrete analytic and diagnostic outcomes. The second forward primer also enables identification of SA without an SSCmec resistance cassette via positive amplification of PCR product between second forward primer and reverse primer (Product 2), without showing amplification of the product from the primer that binds (overlaps) the junction region directly.

In one embodiment the method of the present invention is characterized in that the second forward primer comprises a sequence according to SEQ ID Nr. 2.

In one embodiment the method of the present invention is characterized in that a reverse primer is used, which hybridizes to the SA genome and represents a joint primer for the amplification reactions with both forward primers as described herein.

In one embodiment the method of the present invention is characterized in that the reverse primer comprises a sequence according to SEQ ID Nr. 3.

In one embodiment the method of the present invention is characterized in that two amplification reaction products are formed, namely
  a. A product that results from amplification between the one or more first forward primer(s) and the reverse primer (Product 1), and
  b. a product that results from amplification between the second forward primer and the reverse primer (Product 2).

The present invention therefore enables differentiation between:
  methicillin resistant, coagulase positive MRSA (via positive PCR amplification of PCR product between the first forward primer and reverse primer (Product 1), and preferably in addition to positive amplification of PCR product between second forward primer and reverse primer (Product 2)),
  methicillin resistant, coagulase negative *Staphylococcus* (CNS) strains (via indirect exclusion of CNS, because the first forward and reverse primers of the present invention do not hybridize to CNS sequences, so an MRSA-specific system is provided), and
  SA without SSCmec resistance cassette (indirect detection, via positive amplification of PCR product between second forward primer and reverse primer (Product 2) and absence of amplification of PCR product between the first forward primer and reverse primer (Product 1)).

The invention therefore also relates to a method for differentiating between methicillin resistant, coagulase positive (MRSA) strains and methicillin resistant, coagulase negative *Staphylococcus* (CNS) strains.

The invention thereby provides a surprising and unexpected combination of advantages until now not described in the prior art. The present invention also effectively solves two disadvantages of the prior art, namely a) the limitation of previous methods that could only detect one MRSA variant and b) the fact that CNS were also amplified as false positives. The present invention, as described by both the independent claims and preferred embodiments, in particular with reference to SEQ ID No. 1, provides a method capable of detecting multiple MRSA variants and additionally provides no background or false positive amplification of CNS sequences. That the preferred sequence SEQ ID No. 1 enabled such a solution could neither have been expected nor derived from the prior art. This effect(s) arises particularly for SEQ ID No. 1, whereby Primers 1 and 5 from EP 1529847 show comparatively an absence or a significantly reduced extent of these advantages.

In one embodiment the method of the present invention is characterized in that multiplex polymerase chain reaction (PCR) is carried out.

In one embodiment the method of the present invention is characterized in that the following PCR steps are carried out:
  a. denaturation of the nucleic acid to be detected,
  b. addition of the primers and subsequent hybridization of the primer to target sequence,
  c. amplification of the nucleic acid to be detected,
  d. real-time detection of the nucleic acid to be detected in separate channels.

In one embodiment the method of the present invention is characterized in that detection of the mecA or mecA-equivalent gene is carried out via a specific amplification reaction in addition to the amplification reactions described above.

mecA identification is additionally carried out in a preferred embodiment, whereby "mecA" encompasses known and as yet unknown mecA and mecA-variant sequences that provide a mecA or mecA-analagous function. The mecA gene within the SCCmec cassette is known to allow a bacterium such as MRSA to be resistant to antibiotics such as methicillin, penicillin, erythromycin, tetracycline and other penicillin-like antibiotics. The mecA gene does not allow the ringlike structure of penicillin-like antibiotics to attack the enzymes that help form the cell wall of the bacterium (transpeptidases), and hence the bacteria is allowed to replicate as normal. The gene encodes aprotein PBP2A (Penicillin binding protein 2A). PBP2A has a low affinity for beta-lactam antibiotics such as methicillin and penicillin. This enables transpeptidase activity in the presence of beta-lactams, preventing them from inhibiting cell wall synthesis. The term mecA according to the present invention therefore also encompasses mecA-variants or analogues that perform mecA-equivalent function. One such example of an mecA-analogue is mecC (see Laurent F, Chardon H, et al, MRSA harboring mecA variant gene mecC, France. Emerg Infect Dis, 2012 September as a reference). A divergent mecA homolog (mecC or mecALGA251, in reference to LGA251 isolates from which it was characterized) has recently been described in a staphylococcal cassette chromosome mec named type XI. mecC has <63% aa identity with PBP2a encoded by mecA and was described in S. aureus and/or coagulase-negative staphylococci. The mecA homolog mecC provides analogous function and has been detected in bacteria from dairy cattle in England and humans in England, Scotland, and Denmark. Therefore in a preferred embodiment the detection of mecC is also encompassed in the present invention. In one embodiment the term mecA encompasses mecC.

In one embodiment the method of the present invention is characterized in that an internal amplification control is carried out via a specific amplification reaction in addition to the amplification reactions described above. In one embodiment the method of the present invention is characterized in that up to four amplification reaction products are formed. In one embodiment the method of the present invention is characterized in that the method comprises of individual detection of each of the amplification reaction products. In one embodiment the method of the present invention is characterized in that the method comprises real-time detection of quadruplex PCR in separated channels.

A further aspect of the invention relates to a diagnostic kit for carrying out the amplification reaction(s) as described above comprising one or more oligonucleotide(s) with a sequence according to SEQ ID Nr. 1, 2 or 3 and at least one enzyme.

A further aspect of the invention relates to an isolated synthetic oligonucleotide comprising the sequence according to SEQ ID Nr. 1 or a functionally analogous sequence, comprising a nucleotide sequence with more than 80% sequence identity, preferably more than 90% sequence identity, to SEQ ID Nr. 1.

A further aspect of the invention relates to an isolated synthetic oligonucleotide comprising the sequence according to SEQ ID Nr. 2 or a functionally analogous sequence, comprising a nucleotide sequence with more than 80% sequence identity, preferably more than 90% sequence identity, to SEQ ID Nr. 2.

A further aspect of the invention relates to an isolated synthetic oligonucleotide comprising the sequence according to SEQ ID Nr. 3 or a functionally analogous sequence, comprising a nucleotide sequence with more than 80% sequence identity, preferably more than 90% sequence identity, to SEQ ID Nr. 3.

A further aspect of the invention relates to the use of one or more oligonucleotide(s) described above in a method described above.

The invention further relates to functionally analogous sequences of the DNA sequences provided in Table 1, including primers and probes used herein. Functionally analogous sequences are those that although exhibiting differences in DNA sequence, exhibit similar properties so that the function of the DNA sequence in the context of the present invention is maintained. Functionally analogous sequences can be tested by one skilled in the art without inventive effort in light of the information provided within the application, for example by testing Tm or hybridization properties in the context of the PCR method described.

DETAILED DESCRIPTION OF THE INVENTION

The amplification reaction of the method for detecting MRSA of the present invention is characterised in a preferred embodiment in that 2 PCR products are formed. The first product, which is amplified using the first forward primer (junction-primer) and the reverse primer, provides a stable and reliable detection of all junction sites (integration site of SSCmec cassette in SA genome). This represents a surprising and beneficial aspect of the invention.

One of the significant disadvantages of the methods of the prior art is that their failure rate is very high due to the sequence variation between the various SSCmec cassettes. Because such variation exists in the natural population of MRSA strains (at the filing date of this application more than 8 sequence variants of the SSCmec cassette had been discovered) the primers designed to bind across or near to the junction site would not reliably hybridize to their target DNA sequence, thereby providing false negative results.

The present invention represents an effective solution to this problem, whereby the first primer, with a preferred Tm of 60° C., binds specifically and reliably regardless of the sequence variation of the SSCmec cassettes known to exist. This property (Tm) applies preferably to the sequence according to SEQ ID Nr. 1, which exhibits reliable binding properties regardless of sequence variation in the SSCmec cassette. The Tm of the one or more forward primers is itself is of great importance to the invention as claimed, in some cases independently of the specific sequence. Too low Tm of the primer involved may for example lead to non-specific products caused by a high number of base pair mismatches and difficulties in forming stable hybridisation under normal annealing conditions.

The annealing temperature ($T_a$) chosen for the amplification depends on the length and composition of the primer(s). Generally, an annealing temperature about 2 to 7° C., for example 5° C., below the lowest $T_m$ of the pair of primers is used. Such a strategy may be employed for the present method. Slightly higher Ta may also be applied in order to increase the stringency of the reaction, for example Ta of approximately the same Tm as the primers may be applied. Therefore, the Ta in the amplification reaction as described herein may be, in one embodiment, from 50 to 65° C., preferably from 55 to 65, more preferably approximately 60° C. Other Ta values may be used depending on the primers applied.

The second PCR product detects all SA strains. The combination of the two reactions provides a synergistic effect, in that only 3 primers are required to provide a stable detection system that only detects MRSA without detecting CNS, which is independent of the sequence variation possible in and around the junction region.

The invention further relates to all sequences according to Table 1.

TABLE 1

Preferred sequences of the present invention

| SEQ ID Nr. | Description | Sequence (5'-3') |
|---|---|---|
| 1 | First forward primer | CATCATTTATGGTATGCTTCTCCAC |
| 2 | Second forward primer | TGTACACTTGTTCAATTAACACAACC |

TABLE 1-continued

Preferred sequences of the present invention

| SEQ ID Nr. | Description | Sequence (5'-3') |
|---|---|---|
| 3 | Reverse primer | CAACGCAGTAACTATGCACTATCA |
| 4 | SCC-mec-Probe—relates to the reverse complement sequence of the target sequence provided in Figure 9 | FAM-TGTATAGAGCGTTTAAGATTATGC-IBFQ-ZEN |
| 5 | Staphylococcus aureus-Probe—relates to the reverse complement sequence of the target sequence provided in Figure 9 | Rox-ACATTTCCACATCAAATGATGCG-BHQ2 |

| mecA-system | | |
|---|---|---|
| 6 | forward primer | CGGTCTAAAATTTTACCACGTTC |
| 7 | reverse primer | GGATCATAGCGTCATTATTCCA |
| 8 | Probe 3 | Cy5-ATGCAGAAAGACCAAAGCATACA-BHQ2 |

| mecC-system | | |
|---|---|---|
| 9 | forward primer | TGGAGACCAGACGTTATAGTACCT |
| 10 | reverse primer | GATTTTGCCACGTTCTGATTTTA |
| 11 | Probe 4 | Cy5-TTCTGTCCATTTTTCAAACCAGG-BHQ2 |

| SSC-mec types | | |
|---|---|---|
| 12 | type I (AB014431) | CATTACTTATGATAAGCTTCTCCACGCATAATCTTAAATGCTCTATACACTTGCTCAATTAACACAACCCGCATCATTTGATGTGGGAATGTCATTTTGCTGAATGATAGTGCGTAGTTACTGCGTTG |
| 13 | type II (AB063172) | CATCATTTATGATATGCTTCTCCACGCATAATCTTAAATGCTCTATACACTTGTTCAATTAACACAACCCGCATCATTTGATGTGGGAATGTCATTTTGCTAAATGATAGTGCATAGTTACTGCGTTG |
| 14 | type III (AB425427) | TTTTATTTGTGGTACGCTTCTCCACGCATAATCTTAAATGCTCTGTACACTTGTTCAATTAACACAACCCGCATCATTTGATGTGGGAATGTCATTTTGCTGAATGATAGTGCGTAGTTACTGCGTTG |
| 15 | type IV (FR753166) | CATCACTTATGATACGCTTCTCCACGCATAATCTTAAATGCTCTATACACTTGCTCAATTAACACAACCCGCATCATTTGATGTGGGAATGTCATTTTGCTGAATGATAGTGCGTAGTTACTACGTTG |
| 16 | type V (GQ902038) | TTTTATTTATGATACGCTTCTCCACGCATAATCTTAAATGCTCTATACACTTGCTCAATTAACACAACCCGCATCATTTGGTGTGGGAATGTCATTTTGCTGAATGATAGTGCGTAGTTACTGCGTTG |

In a preferred embodiment all 3 primers exhibit a Tm of approx. 60° C. The Tm of the primers according to SEQ ID Nr. 1, 2 and 3 are preferably between 55° and 65° C., preferably between 56° and 64° C., more preferably between 57° and 63° C., and most preferably is 60° C. In the meaning of the invention these ranges also include the values 55.0, 55.1, 55.2, 55.3, 55.4, 55.5, 55.6, 55.7, 55.8, 55.9, 56.0, 56.1, 56.2, 56.3, 56.4, 56.5, 56.6, 56.7, 56.8, 56.9, 57.0, 57.1, 57.2, 57.3, 57.4, 57.5, 57.6, 57.7, 57.8, 57.9, 58.0, 58.1, 58.2, 58.3, 58.4, 58.5, 58.6, 58.7, 58.8, 58.9, 59.0, 59.1, 59.2, 59.3, 59.4, 59.5, 59.6, 59.7, 59.8, 59.9, 60.0, 60.1, 60.2, 60.3, 60.4, 60.5, 60.6, 60.7, 60.8, 60.9, 61.0, 61.1, 61.2, 61.3, 61.4, 61.5, 61.6, 61.7, 61.8, 61.9, 62.0, 62.1, 62.2, 62.3, 62.4, 62.5, 62.6, 62.7, 62.8, 62.9, 63.0, 63.1, 63.2, 63.3, 63.4, 63.5, 63.6, 63.7, 63.8, 63.9, 64.0, 64.1, 64.2, 64.3, 64.4, 64.5, 64.6, 64.7, 64.8, 64.9 and 65° C., and all other values falling within the range.

Surprisingly, the first forward primer, preferably according to SEQ ID Nr. 1, shows stable and reliable hybridization to all known variants of the SSCmec cassette, therefore allowing this simple, efficient and reliable system to be applied regardless of which particular SSCmec cassette may be responsible for the resistance in the MRSA.

The inventive properties of SEQ ID Nr. 1 are better illustrated in Table 2 via a comparison with the known and disadvantageous system of EP 1529847.

avoidance of false positive results, thereby avoiding amplification of unwanted CNS strains and providing reliable detection of MRSA strains. It would also have been impossible to assume from the prior art that this particular sequence modification would lead to such beneficial properties.

These features of SEQ ID Nr. 1 work together in a synergistic manner, providing enhanced hybridization in light of possible sequence variation in target sequence, enhanced specificity and an optimal Tm, in order to enable a novel and surprising improvement over the primers known in the art.

Methicillin resistant, coagulase negative *Staphylococcus* (CNS) strains relate to *Staphylococcus* strains that do not possess or actively express the coagulase gene, which codes for an enzyme that causes blot clot formation. Examples of CNS are *S. epidermis* and *S. warneri*.

Methicillin, also known as Meticillin, is a narrow-spectrum beta-lactam antibiotic of the penicillin class. Like other beta-lactam antibiotics, methicillin acts by inhibiting the synthesis of bacterial cell walls.

The present invention relates primarily to PCR-based methods. PCR as such is known in the art and modifications of, or particular variations on, known PCR reactions or

TABLE 2

Sequence alignment between SEQ ID NO 1 and the analogous primers (1 and 5) from EP 1529847.

| Description | Sequence |
| --- | --- |
| SEQ ID Nr. 1 | CATCATTTATGGTATGCTTCTCCAC |
| Identity | ------ \|\|\|\|\|-\|\|\|\|\|\|\|\|\|\|\|-- |
| Primer 5 from EP 1529847 | TTATGATATGCTTCTCC (SEQ ID NO 17) |
| SEQ ID Nr. 1 | CATCATTTATGGTATGCTTCTCCAC |
| Identity | ------ \|\|\|\|\|-\|\|-\|\|\|\|\|\|\|\|-- |
| Primer 1 from EP 1529847 | TTATGATAAGCTTCTCC (SEQ ID NO 18) |

The preferred first forward primer of the present invention differs from the primers known in EP 1529847 in various respects. Firstly, there is a significant 5' extension present in the primer of SEQ ID Nr. 1. The 5' extension has been developed in order to improve the hybridization capabilities of the primer in light of the varying sequence identity of the SSCmec cassettes known in the art. It was unexpected, that this particular sequence, especially the 5' extension compared to the primers known in EP 1529847, would enable a single primer to be used in the identification of potentially all known MRSA strains. The corresponding advantage of reduced complexity in multiplex systems (fewer primers) or reduced PCR reactions leads to both technical and secondary beneficial effects, such as financial success due to increased reliability and reduced cost. Due to this sequence, and due to the Tm of the primer, the primer of SEQ ID Nr. 1 shows stable and reliable hybridization to various known SSCmec cassettes.

The 3' extension also represents a significant improvement compared to the sequences disclosed in EP 1529847. With the two additional nucleotides at the 3' end the inventor has provided an enormous improvement in the specificity of the primer. This specificity can for example also lead to the methods are included in the scope of the invention when used to carry out the method described herein.

PCR relies on thermal cycling, consisting of cycles of repeated heating and cooling of the reaction for DNA melting (separation of the double strand) and enzymatic replication of the DNA. Primers relate to short DNA oligonucleotides that contain sequences complementary to the target region. A DNA polymerase is applied that facilitates selective and repeated amplification. As PCR progresses, the DNA generated is used as a template for replication, enabling a chain reaction in which the DNA template is exponentially amplified.

Alternative nucleic acid amplification technologies may also be applied that are known in the field of molecular biology. The polymerase chain reaction (PCR) is the most widely used method for DNA amplification, however, PCR requires a thermocycling machine to separate two DNA strands and then amplify the required fragment. Novel developments in molecular biology demonstrate the possibility of amplifying DNA in isothermal conditions without the need of a thermocycling apparatus. Isothermal approaches for amplification are therefore also included in the scope of the present invention. There are several types of isothermal nucleic acid amplification methods such as transcription mediated amplification, nucleic acid sequence-based amplification, signal mediated amplification of RNA technology, strand displacement amplification, rolling circle amplification, loop-mediated isothermal amplification of DNA, isothermal multiple displacement amplification, helicase-dependent amplification, single primer isothermal amplification, and circular helicase-dependent amplification (see Gill et al, Nucleosides Nucleotides Nucleic Acids. 2008 March; 27(3):224-43, for a review).

Loop mediated isothermal amplification (LAMP) is one example of isothermal amplification that relates to a single tube technique for the amplification of DNA. LAMP enables nucleic acid amplification which uses a single temperature incubation thereby obviating the need for expensive thermal cyclers. Detection of amplification product can be by photometry for turbidity caused by increasing quantity of Magnesium pyrophosphate in solution or with addition of SYBR green, a color change can be seen without equipment. Also in-tube detection of DNA amplification is possible using manganese loaded calcein which starts fluorescing upon complexation of manganes by pyrophosphate during in vitro DNA synthesis. LAMP is a relatively new DNA amplification technique, which due to its simplicity, ruggedness, and low cost could provide major advantages. In LAMP, the target sequence is amplified at a constant temperature of 60-65° C. using either two or three sets of primers and a polymerase with high strand displacement activity in addition to a replication activity. LAMP can also be quantitative.

The term "DNA polymerase" describes an enzyme frequently used in the polymerase chain reaction. Such enzymes include the Taq polymerase, a thermostable DNA polymerase named after the thermophilic bacterium *Thermus aquaticus*. Other thermostable polymerases are e.g. the Pfu DNA polymerase, which has been isolated from the hyperthermophilic bacterium *Pyrococcus furiosus* and has a 3'-5' exonuclease proofreading activity. Two DNA polymerases are mentioned exemplarily but do not represent limitations to the invention.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an inducing agent such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method. For example, for diagnostics applications, depending on the complexity of the target sequence, the oligonucleotide primer typically contains 15-25 or more nucleotides, although it may contain fewer nucleotides. Preferred primers are provided in Table 1.

One preferred embodiment relates to real time PCR (RT-PCR) or quantitative RT-PCR (qRT-PCR), as it allows the quantification of the amplified target in real-time. The term "real-time PCR" is intended to mean any amplification technique which makes it possible to monitor the progress of an ongoing amplification reaction as it occurs (i.e. in real time). Data is therefore collected during the exponential phase of the PCR reaction, rather than at the end point as in conventional PCR. Measuring the kinetics of the reaction n the early phases of PCR provides distinct advantages over traditional PCR detection. In real-time PCR, reactions are characterized by the point in time during cycling when amplification of a target is first detected rather than the amount of target accumulated after a fixed number of cycles. The higher the starting copy number of the nucleic acid target, the sooner a significant increase in fluorescence is observed. Traditional PCR methods may also be applied, and use separation methods, such as agarose gels, for detection of PCR amplification at the final phase of or end-point of the PCR reaction. For qRT-PCR no post-PCR processing of the unknown DNA sample is necessary as the quantification occurs in real-time during the reaction. Furthermore, an increase in reporter fluorescent signal is directly proportional to the number of amplicons generated.

In another preferred embodiment the invention relates to a method, wherein the amplification is a multiplex PCR with more than one pair of primers. The multiplex PCR is a variant of the standard PCR in which two or more loci are simultaneously amplified in the same reaction, by including more than one pair of primers in the reaction.

The primers herein are selected to be "substantially" complementary to the different strands of each specific sequence to be amplified. This means that the primers must be sufficiently complementary to hybridize with their respective strands. Therefore, the primer sequences do not need to reflect the exact complementary sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer.

Hybridization is the process of establishing a non-covalent, sequence-specific interaction between two or more complementary strands of nucleic acids into a single hybrid, which in the case of two strands is referred to as a duplex or DNA double strand in the case of DNA. Oligonucleotides, DNA, or RNA will bind to their complement under normal conditions, so two perfectly complementary strands will bind to each other readily. Due to the different molecular geometries of the nucleotides, a single inconsistency between the two strands will make binding between them less energetically favourable. The hybrids may be dissociated by thermal denaturation, also referred to as melting. Here, the solution of hybrids is heated to break the hydrogen bonds between nucleic bases, after which the two strands separate. In the absence of external negative factors, the processes of hybridization and melting may be repeated in succession indefinitely, which lays the ground for polymerase chain reaction.

For multiple copies of DNA molecules, the melting temperature (Tm) is generally defined as the temperature at which half of the DNA strands are in the double-helical state and half are in the random coil states. The melting temperature depends on both the length of the molecule, and the specific nucleotide sequence composition of that molecule. The melting temperature of an oligonucleotide primer can be calculated using various methods.

Theoretical and/or empirical measurements can be made for determining the Tm of primers. Examples for theoretical measurement obtained from the Promega website relate to:

$T_m$=4° C.×(number of G's and C's in the primer)+2° C.×(number of A's and T's in the primer)

This formula is valid for oligos <14 bases and assumes that the reaction is carried out in the presence of 50 mM monovalent cations. For longer oligos, the formula below is used:

$T_m$=64.9° C.+41° C.×(number of G's and C's in the primer−16.4)/N (where N is the length of the primer)

For example, Promega's T7 Promoter Primer (TAATAC-GACTCACTATAGGG) is a 20 mer composed of 5 T's, 7 A's, 4 C's, and 4 G's. Thus, its melting temperature is calculated:

64.9° C.+41° C.×(8−16.4)/20=47.7° C.

Examples of empirical determination of Tm of a primer relate to determining the actual melting point, for example using a thermostatted cell in a UV spectrophotometer. If temperature is plotted vs. absorbance, an S-shaped curve with two plateaus will be observed. The absorbance reading halfway between the plateaus corresponds to Tm (obtained from Sigma Aldrich). Other useful references for Tm calculation are Wallace, R. B.; Shaffer, J.; Murphy, R. F.; Bonner, J.; Hirose, T.; Itakura, K. Nucleic Acids Res. 6, 3543 (1979) and Howley, P. M; Israel, M. F.; law, M-F.; Martin, M. A. J. Biol. Chem. 254, 4876.

A preferred method for calculating Tm of the primers is according to the software Primer Premier 5. According to this method melting temperatures are based on nearest neighbour thermodynamic theory. The formulas are from the paper by Freier et al (1986 "Improved free-energy parameters for predictions of RNA duplex stability" Proc Natl Acad Sci USA 83 9373-9377). These are highly accurate nearest neighbour based Tm calculations. Several corrections have been incorporated into the formula to yield the most accurate results possible.

$Tm=DH/(DS+R*In(C/4))+16.6 \log([K+]/(1+0.7[K+]))-273.15$

DH is the enthalpy for helix formation. DS is the entropy for helix formation. C is the DNA concentration. [K+] is the salt concentration. DH and DS for the respective oligo are calculated using the values of nearest-neighbour thermodynamics from Breslauer, K. J. (1986 "Predicting DNA duplex stability from the base sequence" Proc Natl Acad Sci USA 83 3746-3750). Since the thermodynamic values calculated by the method of Breslauer are at 1 M Na+, it was necessary to add a term to correct for salt concentration, [K+]. [K+] is calculated using both the monovalent ion concentration and the free Mg2+ concentration. The value of [K+] is determined using the formula:

[K+]=Monovalent ion concentration+4×Sq. root (Free Mg2+ ion concentration)×1000

The salt concentration i.e., [K+] is represented as Total Na+ Equivalent and is updated according to the changes made in either Monovalent ion concentration or Free Mg2+ ion concentration. The default values of Monovalent ion concentration and Free Mg2+ ion concentration are 50.0 mM and 1.5 mM res., which gives a total salt concentration equal to 204.9 mM. In the formulation of Freier et al., c is the total molar concentration of the annealing oligos, when oligos are not self-complementary. It is neither the primer concentration nor the initial template concentration. It is based on the PCR product concentration. Since the concentration of template changes dramatically during the course of the PCR, it is difficult to define the value of "c". It has been empirically determined that setting the value of c=250 pM, gives good results in a wide variety of PCR and sequencing reactions.

According to the methods described above, the Tm of the oligos according to Primer 5 and Primer 1 from EP 1529847 are approximately 38 to 48° C. Primer 5 from EP 1529847 has a Tm of 42.3° C. (according to Primer Premier 5) or 46° C. (according to the 4+2 method, for example from Promega). Primer 1 from EP 1529847 has a Tm of 38.3° C. (according to Primer Premier 5) or 44° C. (according to the 4+2 method, for example from Promega). EP 1529847 discloses that a higher amplimer quantity could be obtained by lowering the annealing temperature to 50° C. Even such a measure is unlikely to provide reliable and specific amplification. With the sequences of Primer 1 and 5 as disclosed it is very surprising that any product at all is generated at either 55° C. or 50° C. as Tm. Increased amounts of template bacteria, in order to improve yields could be applied to produce PCR product, although in practice such an approach is entirely unhelpful for clinical diagnostics. EP 1529847 also discloses using 45° C. as Ta, which may then allow amplification but also increases the risk of non-specific amplification, as described above. Primers 1 and 5 from EP 1529847 therefore do not enable quantitative and reliable application in diagnostic practice.

The Tm of SEQ ID No. 1 of the present invention is approximately 60° C. These values can be confirmed by other methods, for example those of the "applied bio systems" website. Some variation in Tm does occur depending on the method used, but in general, the Tm of any given sequence can be reliably determined with different methods that provide similar outcomes.

The present invention is intended to be applied in clinical diagnostic applications, in particular PCR kits for MRSA diagnosis, which provide a fast and reliable MRSA diagnosis without the need for extensive re-checking and further tests.

The method of the present invention is intended to be carried out using samples obtained from subjects to be tested for the presence of MRSA. Samples to be tested can be obtained via various measures, for example from body fluids of subjects, such as blood or saliva.

Tissue samples, such as skin samples, or nasal secretions may also be obtained and subsequently tested for the presence of MRSA using the invention described herein. Bacterial cultures may also be used, if for example the MRSA has been isolated and cultured before testing.

FIGURES

The figures represent working examples and are not intended to limit the scope of the invention.

FIG. 1

A schematic representation of the mecA cassette junction region is provided in FIG. 1. The positions where the primers hybridize to template DNA is provided. Primers are indicated as arrows (1: first forward primer, 2: second forward primer, 3: reverse primer). The first forward primer with a Tm of preferably 60° C. hybridizes across the junction between SSCmec cassette and SA genome. The PCR products Product 1 and Product 2 are also shown.

FIG. 2

Figure 5:
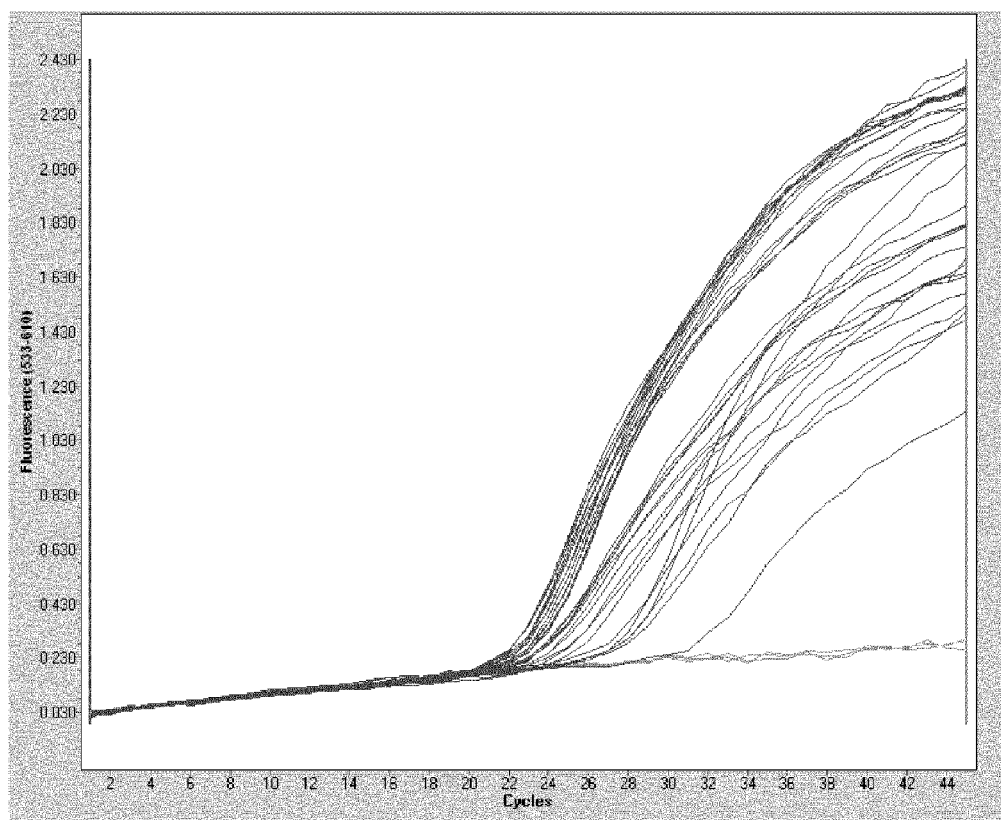
Figure 6:
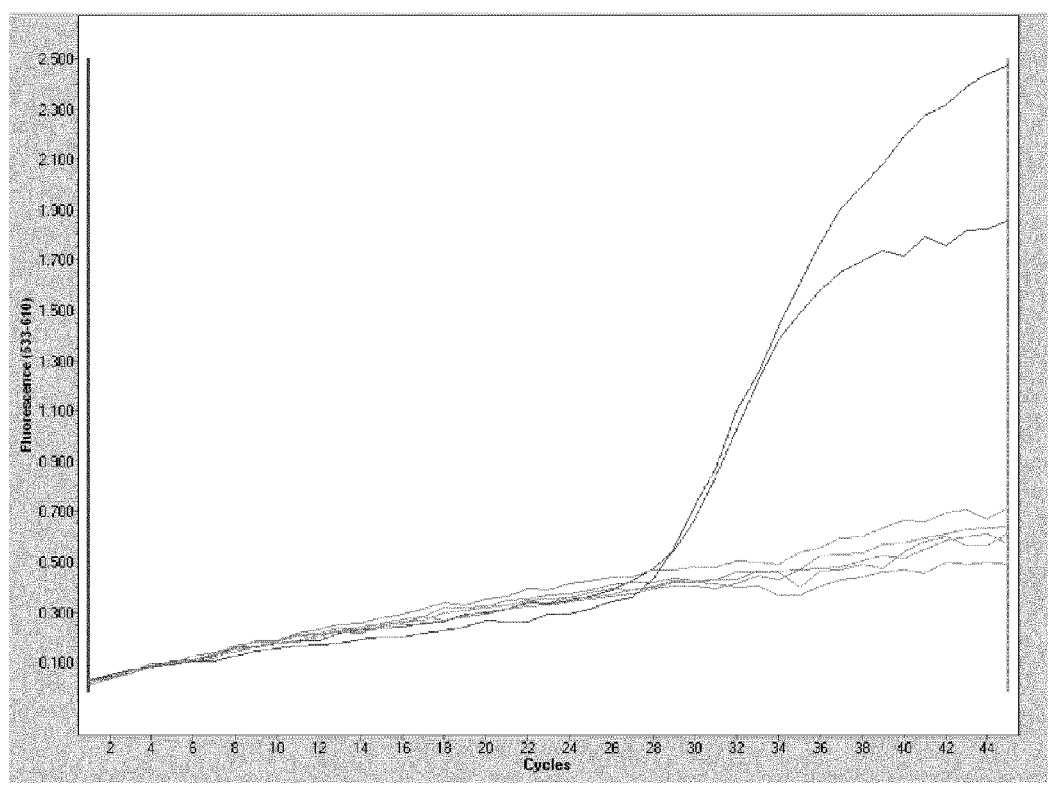
Figure 7:
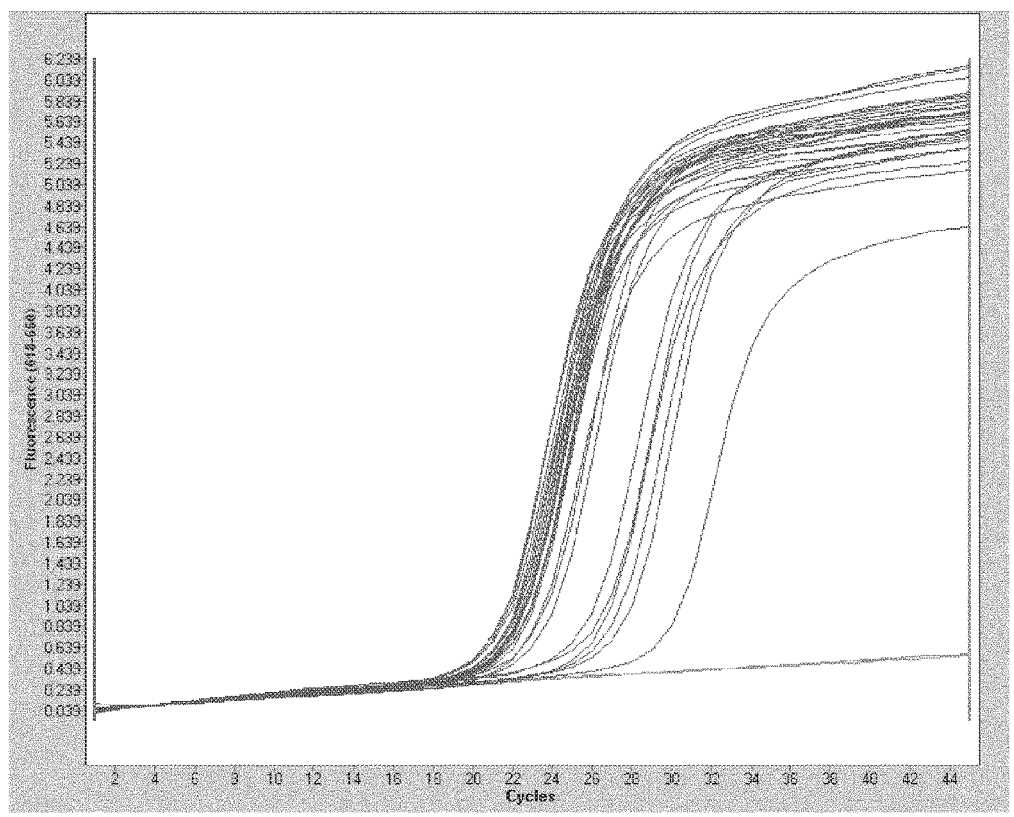
Figure 8:
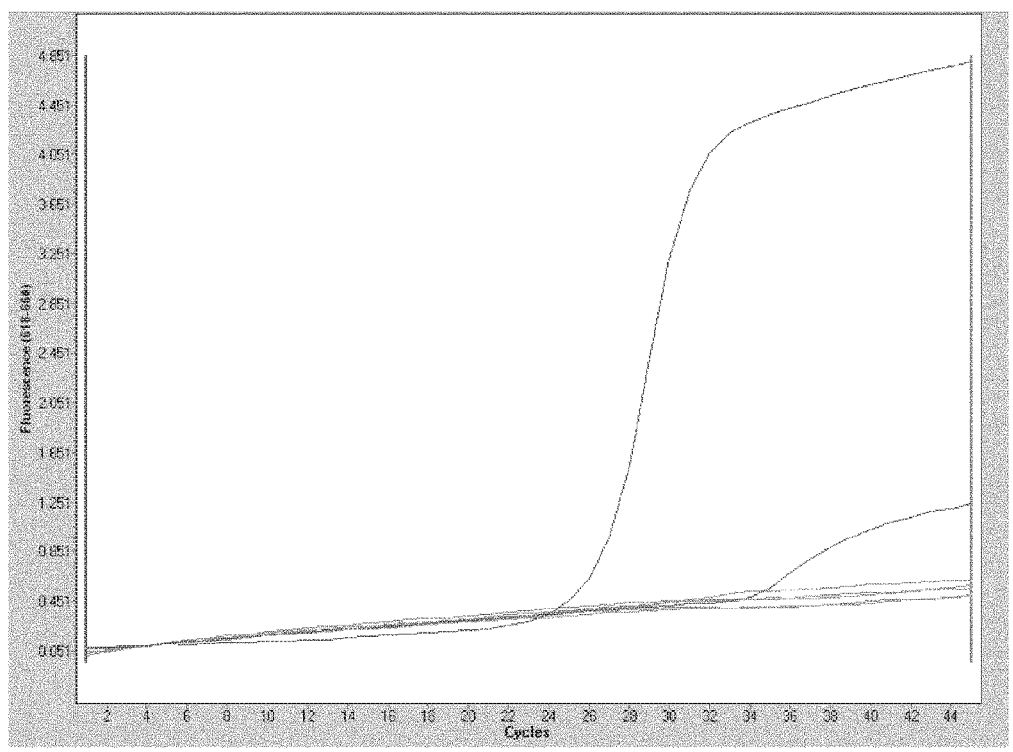

An overview and explanation about the results of the practical experiment is provided. In addition the allocation of the experiment to the respective results shown in FIGS. 3 to 9 is given. Furthermore, in FIG. 2 it is shown that the SSC-mec product is obtained in the amplification reaction, three primers are used and the detection is monitored via channel 510. The graphs are shown in the FIGS. 3 and 4. For the SA product the primers two to three are used, via channel 610 the detection takes place and the results are shown in FIGS. 5 and 6. The mecA product is detected via channel 660 and the results are shown in FIGS. 7 and 8.

FIG. 3

In FIG. 3 the amplification curves for the different MRSA samples are shown. There, dependent on the cycle number (x-axis) the fluorescence intensity of the SSC-mec product (y-axis) is given. The detection takes place via channel 510.

FIG. 4

In FIG. 4 the amplification curves of the positive control and non-MRSA samples are shown. Detection takes place via channel 510.

FIG. 5

In FIG. 5 the amplification curves for the different MRSA samples are shown. There, dependent on the cycle number (x-axis) the fluorescence intensity of the SA product is given (y-axis). The detection takes place via channel 610.

FIG. 6

In FIG. 6 the amplification curves of the positive control and non-MRSA samples are shown. Detection takes place via channel 610.

FIG. 7

In FIG. 7 the amplification curves for the different MRSA samples are shown. There, dependent on the cycle number (x-axis) the fluorescence intensity of the mecA product is given (y-axis). The detection takes place via channel 660.

FIG. 8

In FIG. 8 the amplification curves of the positive control and non-MRSA samples are shown. Detection takes place via channel 660.

FIG. 9

FIG. 9 shows the template sequence for 5 various SCC-mec types. Additionally the accession number is given. Also the primer sequences are provided. Each primer is allocated to the corresponding sequence of the 5 SCC-mec type. The used oligonucleotides do show some differences in comparison to the target sequences. However, it is not essential that absolute sequence identity occurs between primer and template at every nucleotide position. Key criterion for a suitable primer is the possibility to enable hyridisation.

EXAMPLES

The following examples represent a preferred method but are not intended to limit the scope of the invention.

Example 1

The detection reaction is carried out in a quadruplex Real-Time PCR (RT-PCR) system, comprising detection of the two reaction products, in addition to a mecA control amplification and an internal control amplification.

The junction-specific reaction (first forward primer and reverse primer (Product 1)) is measured in the 510-channel, the internal control measured in the 580-channel, the SA-detection reaction (second forward primer and reverse primer (Product 2)) measured in the 610-channel and the mecA detection measured in the 660-channel. Positive identification of methicillin resistant coagulase positive *Staphylococcus aureus* (SA) strains is obtained by positive PCR amplification in the 510, 610 and 660 channels.

In the example a multiplex-real-time PCR with known and unknown samples has been conducted with the LC 480. The three relevant channels are analyzed separately.

Practically, the conducted experiment consists of 2 runs. In the first run all samples analyzed are MRSA. For all known species the SSC-mec type is mentioned in the table below. Otherwise the samples are named with unknown. In the second run only non-MRSA are analyzed and a PTC (positive template control—a synthetic MRSA) is used as comparison. Three channels are analyzed. The results are given in the FIGS. 2 to 7. The Cp-values are compiled in the table below.

MRSA Samples:

| channel | 510 | 610 | 660 |
|---|---|---|---|
| sample | Cp SCC-mec | Cp *S. aureus* | Cp mecA |
| NTC | negative | negative | negative |
| NTC | negative | negative | negative |
| NTC | negative | negative | negative |
| MRSA SCC III | 30 | 35 | 29 |
| MRSA SCC IVc | 22 | 27 | 21 |
| MRSA SCC IVc | 27 | 30 | 24 |
| MRSA SCC I | 28 | 31 | 26 |
| MRSA LA | 28 | 30 | 26 |
| MRSA SCC unknown | 28 | 30 | 26 |
| MRSA SCC unknown | 24 | 25 | 21 |
| MRSA SCC unknown | 23 | 25 | 21 |
| MRSA SCC V | 23 | 25 | 21 |
| MRSA SCC IVd | 22 | 24 | 20 |
| MRSA SCC IVa | 22 | 25 | 20 |
| MRSA SCC unknown | 24 | 25 | 21 |
| MRSA SCC II | 23 | 27 | 21 |
| MRSA SCC V | 24 | 26 | 22 |
| MRSA SCC V | 24 | 26 | 22 |
| MRSA SCC V | 23 | 24 | 21 |
| MRSA SCC unknown | 23 | 25 | 21 |
| MRSA SCC unknown | 23 | 25 | 21 |
| MRSA SCC unknown | 24 | 25 | 21 |
| MRSA SCC unknown | 25 | 26 | 22 |
| MRSA SCC unknown | 23 | 26 | 21 |
| MRSA SCC I | 24 | 27 | 22 |
| MRSA SCC unknown | 25 | 28 | 22 |
| MRSA SCC V | 23 | 25 | 21 |
| MRSA SCC unknown | 23 | 27 | 21 |
| MRSA SCC V | 23 | 25 | 21 |
| MRSA SCC unknown | 25 | 28 | 22 |
| MRSA SCC IVa | 23 | 27 | 21 |
| MRSA SCC II | 24 | 27 | 21 |
| MRSA SCC unknown | 26 | 29 | 23 |
| Positive Control | 26 | 31 | 25 |

Non-MRSA Samples:

| channel | 510 | 610 | 660 |
|---|---|---|---|
| sample | Cp SCC-mec | Cp *S. aureus* | Cp mecA |
| NTC | negative | negative | negative |
| NTC | negative | negative | negative |
| *S. aureus* | negative | 30 | negative |
| *S. cohnii* | negative | negative | negative |
| *S. hominis* | negative | negative | negative |
| *S. epidermidis* | negative | negative | 36 |
| Positive Control | 27 | 30 | 26 |

The Following Concentrations and Volumes of Components Were Used in the Real-Time PCR:

| Component | Volume in μl |
|---|---|
| Water | 6.6 |
| 10 x PCR buffer | 2 |
| Deoxyribonucleotide triphosphates mixture, concentration: 2.5 mM | 2 |
| Bovine serum albumin solution | 1 |
| MgCl$_2$, concentration: 25 mM | 4 |
| Primers 0.5 μl, concentration 10 pmol/μl | 2.5 |
| Probes 0.6 μl, concentration: 5 pmol/μl | 1.8 |
| TAQ-Polymerase, concentration: 10 U/μl | 0.1 |
| Total Volume master mix | 20 |
| DNA sample/extract | 5 |
| Total Volume | 25 |

PCR Temperature Profile

| | | |
|---|---|---|
| Initial denaturation | 95° C. | 5 min |
| Cycling | | 45 cycles |
| Denaturation | 95° C. | 10 sec |
| Annealing/extension | 60° C. | 15 sec |

The invention claimed is:

1. Method for detection of a methicillin resistant coagulase positive *Staphylococcus aureus* (MRSA) strain, said MRSA strain comprising a chromosomal *Staphylococcus mec* (SSCmec) cassette,
the method comprising
performing a sequence specific amplification reaction with one or more first forward primer(s) comprising a sequence according to SEQ ID NO: 1 (CATCATT-TATGGTATGCTT CTCCAC), wherein 5' end of the one or more first forward primer(s) hybridizes to a target DNA sequence within the SSCmec cassette and a 3' end of the one or more first forward primer(s) hybridizes in an adjacent chromosomal DNA
wherein a melting temperature (Tm) of the one or more first forward primer(s) is between 55° and 65° C.

2. The method according to claim 1, wherein the MRSA strain is selected from the group consisting of type I, II, III, V, IV a, IV b, IV c, VII, VIII, IX, X and a combination thereof.

3. The method according to claim 1, wherein a second forward primer is used in the amplification reaction, which hybridizes in the MRSA genome.

4. The method according to claim 3, wherein the second forward primer comprises a sequence according to SEQ ID NO: 2 (TGTACACTTGTTCAATTAACACAACC).

5. The method according to claim 4, wherein, as a further primer, a reverse primer is provided, which hybridizes to the MRSA genome, representing a joint primer for an amplification reaction with the first and second forward primers.

6. The method according to claim 5, wherein the reverse primer comprises a sequence according to SEQ ID NO: 3 (CAACGCAGTAACTATGCACTATCA).

7. The method according to claim 5, producing two amplification reaction products which are
   a. a product that results from amplification between the one or more first forward primer(s) and the reverse primer, and
   b. a product that results from amplification between the second forward primer and the reverse primer.

8. The method according to claim 7 comprising one or two further amplification reactions, wherein up to four amplification reaction products are formed.

9. The method according to claim 1, further comprising identifying a number of MRSA variants via one forward primer or, a number of forward primers that is less than said number of MRSA variants.

10. The method according to claim 1, wherein the MRSA strain to be detected carries a mecA gene in said chromosomal *Staphylococcus mec* (SSCmec) cassette.

11. The method according to claim 10, wherein detection of the mecA gene is carried out via a further specific amplification reaction.

12. The method according to claim 1, wherein an internal amplification control is carried out via a further specific amplification reaction.

13. The method according to claim 1, further comprising differentiating between methicillin resistant, coagulase positive MRSA strains and methicillin resistant, coagulase negative *Staphylococcus* (CNS) strains.

14. The method according to claim 1 comprising performing the amplification reaction with 3, 2 or 1 forward primer (s).

15. The method according to claim 1, comprising performing the amplification reaction with 1 forward primer.

16. The method according to claim 1, wherein the melting temperature (Tm) of the one or more first forward primer(s) is between 56° and 64° C., between 57° and 63° C. or is 60° C.

17. The method of claim 1, wherein the forward primer(s) consists of the sequence according to SEQ ID NO: 1.

* * * * *

SEQUENCE LISTING

<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1
catcatttat ggtatgcttc tccac         25

<210> SEQ ID NO 2
<211> LENGTH: 26
<212> TYPE: DNA
<213> ORGANISM: Artificial Sequence
<220> FEATURE:
<223> OTHER INFORMATION: primer

<400> SEQUENCE: 2
tgtacacttg ttcaattaac acaacc        26

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
caacgcagta actatgcact atca          24

<210> SEQ ID NO 4
<211> LENGTH: 24
<212> TYPE: DNA
<213> ORGANISM: Staphylococcus aureus

<400> SEQUENCE: 4
tgtatagagc gtttaagatt atgc          24

<210> SEQ ID NO 5
<211> LENGTH: 23
<212> TYPE: DNA
<213> ORGANISM: Staphylococcus aureus

<400> SEQUENCE: 5
acatttccac atcaaatgat gcg           23

```
<210> SEQ ID NO 6
<211> LENGTH: 23
<212> TYPE: DNA
<213> ORGANISM: Staphylococcus aureus

<400> SEQUENCE: 6
cggtctaaaa ttttaccacg ttc                                              23

<210> SEQ ID NO 7
<211> LENGTH: 22
<212> TYPE: DNA
<213> ORGANISM: Staphylococcus aureus

<400> SEQUENCE: 7
ggatcatagc gtcattattc ca                                               22

<210> SEQ ID NO 8
<211> LENGTH: 23
<212> TYPE: DNA
<213> ORGANISM: Staphylococcus aureus

<400> SEQUENCE: 8
atgcagaaag accaaagcat aca                                              23

<210> SEQ ID NO 9
<211> LENGTH: 24
<212> TYPE: DNA
<213> ORGANISM: Staphylococcus aureus

<400> SEQUENCE: 9
tggagaccag acgttatagt acct                                             24

<210> SEQ ID NO 10
<211> LENGTH: 23
<212> TYPE: DNA
<213> ORGANISM: Staphylococcus aureus

<400> SEQUENCE: 10
gattttgcca cgttctgatt tta                                              23

<210> SEQ ID NO 11
<211> LENGTH: 23
<212> TYPE: DNA
<213> ORGANISM: Staphylococcus aureus

<400> SEQUENCE: 11
ttctgtccat ttttcaaacc agg                                              23

<210> SEQ ID NO 12
<211> LENGTH: 128
<212> TYPE: DNA
<213> ORGANISM: Staphylococcus aureus

<400> SEQUENCE: 12
cattacttat gataagcttc tccacgcata atcttaaatg ctctatacac ttgctcaatt      60
aacacaaccc gcatcatttg atgtgggaat gtcattttgc tgaatgatag tgcgtagtta     120
ctgcgttg                                                             128

<210> SEQ ID NO 13
<211> LENGTH: 128
<212> TYPE: DNA
<213> ORGANISM: Staphylococcus aureus
```

```
<400> SEQUENCE: 13
catcatttat gatatgcttc tccacgcata atcttaaatg ctctatacac ttgttcaatt    60
aacacaaccc gcatcatttg atgtgggaat gtcattttgc taaatgatag tgcatagtta   120
ctgcgttg                                                            128

<210> SEQ ID NO 14
<211> LENGTH: 128
<212> TYPE: DNA
<213> ORGANISM: Staphylococcus aureus

<400> SEQUENCE: 14
ttttatttgt ggtacgcttc tccacgcata atcttaaatg ctctgtacac ttgttcaatt    60
aacacaaccc gcatcatttg atgtgggaat gtcattttgc tgaatgatag tgcgtagtta   120
ctgcgttg                                                            128

<210> SEQ ID NO 15
<211> LENGTH: 128
<212> TYPE: DNA
<213> ORGANISM: Staphylococcus aureus

<400> SEQUENCE: 15
catcacttat gatacgcttc tccacgcata atcttaaatg ctctatacac ttgctcaatt    60
aacacaaccc gcatcatttg atgtgggaat gtcattttgc tgaatgatag tgcgtagtta   120
ctacgttg                                                            128

<210> SEQ ID NO 16
<211> LENGTH: 128
<212> TYPE: DNA
<213> ORGANISM: Staphylococcus aureus

<400> SEQUENCE: 16
ttttatttat gatacgcttc tccacgcata atcttaaatg ctctatacac ttgctcaatt    60
aacacaaccc gcatcatttg gtgtggaaat gtcattttgc tgaatgatag tgcgtagtta   120
ctgcgttg                                                            128

<210> SEQ ID NO 17
<211> LENGTH: 17
<212> TYPE: DNA
<213> ORGANISM: Artificial Sequence
<220> FEATURE:
<223> OTHER INFORMATION: primer

<400> SEQUENCE: 17
ttatgatatg cttctcc                                                   17

<210> SEQ ID NO 18
<211> LENGTH: 17
<212> TYPE: DNA
<213> ORGANISM: Artificial Sequence
<220> FEATURE:
<223> OTHER INFORMATION: primer

<400> SEQUENCE: 18
ttatgataag cttctcc                                                   17
```